United States Patent [19]
Rosenfeld

[11] Patent Number: 5,622,181
[45] Date of Patent: Apr. 22, 1997

[54] METHOD AND SYSTEM FOR DETECTION OF MEMORY DEFICIENCY MALINGERING UTILIZING BRAIN WAVES

[76] Inventor: J. Peter Rosenfeld, 975 Vernon Ave., Winnetka, Ill. 60093

[21] Appl. No.: 340,119

[22] Filed: Nov. 15, 1994

[51] Int. Cl.⁶ .................................................... A61B 5/04
[52] U.S. Cl. ........................................... 128/731; 128/898
[58] Field of Search ...................................... 128/731, 732, 128/733, 745, 746, 898; 364/413.05

[56] References Cited

U.S. PATENT DOCUMENTS

| | | | |
|---|---|---|---|
| 4,932,416 | 6/1990 | Rosenfeld | 128/731 |
| 5,113,870 | 5/1992 | Rosenfeld | 128/731 |
| 5,137,027 | 8/1992 | Rosenfeld | 128/731 |

OTHER PUBLICATIONS

P3–enhanced 'MDMT' (matching–to–sample) test in detection of simulated amnesia: individual diagnostic test comparison; Author(s): Rosenfeld et al.; Aug. 1994.

Neuropsychological Assessment and Malingering: A Critical Review of Past and Present Strategies; *Archives of Clinical Neuropsychology*, vol. 9, No. 6, pp. 501–552; Author(s): Nies et al.; 1994.

Refining the Forced–Choice Method for the Detection of Malingering, *Journal of Clinical and Experimental Neuropsychology*, vol. 11, No. 6, pp. 967–974; Author(s): Hiscock et al.; 1989.

Detecting Simulated Memory Impairment: Comparison of the Rey Fifteen–Item Test and the Hiscock Forced–Choice Procedure, *The Clinical Neuropsychologist*, vol. 8, No. 3, pp. 283–294; Author(s): Guilmette et al.; 1994.

Taking the Stand: Issues and Strategies in Forensic Neuropsychology, *The Clinical Neuropsychologist*, vol. 5, No. 3, pp. 197–219; Author(s): Guilmette et al.; 1991.

Event–related brain potential evidence for a verbal working memory deficit in multiple sclerosis; *Brain*, 117, 289–305; Author(s): Ruchkin et al.; 1994.

*Primary Examiner*—Angela D. Sykes
*Assistant Examiner*—Samuel Gilbert
*Attorney, Agent, or Firm*—Brinks Hofer Gilson & Lione

[57] ABSTRACT

A system and method for detecting memory deficiency malingering in a subject. The subject is presented with a series of trials wherein each trial includes display of a sample stimulus, followed by display of a test stimulus. In some of the trials the test stimulus matches the sample stimulus and in others of the trials the test stimulus does not match the sample stimulus. The subject's brain waves are measured and recorded during at least some of the display of the test stimuli. The subject indicates with respect to at least some of the test stimuli whether the test stimulus matches or does not match the sample stimulus. Memory deficiency malingering can be determined by comparing the indication from the subject to the measured brain waves of the subject.

26 Claims, 5 Drawing Sheets

Microfiche Appendix Included
(1 Microfiche, 19 Pages)

METHOD AND SYSTEM FOR DETECTION OF MEMORY DEFICIENCY MALINGERING UTILIZING BRAIN WAVES

MICROFICHE APPENDIX

Included is one microfiche appendix including 19 total frames.

BACKGROUND OF THE INVENTION

The present invention relates to a method and system for determining memory deficiency malingering.

It is sometimes required to test a person's memory. For example, occasionally a person who has suffered an accident or head injury asserts that he is experiencing memory problems. This may arise in the context of a claim to an insurance company or in personal injury litigation. In such situations, a memory test may be useful to determine whether the person actually is experiencing memory difficulties or is feigning memory problems for the purpose of financial gain. The feigning or exaggeration of memory impairment by individuals who do not in fact have memory problems is referred to as "malingering".

Various neuropsychological tests have been developed that can be used to assess a person's memory. Some tests are specially designed to test for short term memory deficiencies that may be associated with head injury accidents. The purpose of such tests is to determine whether the subject actually has a memory deficiency or is faking.

A related test is the forced choice procedure test (see, Hiscock & Hiscock "Refining the forced-choice method for the detection of malingering", *Journal of Clinical and Experimental Neuropsychology*, 11, 967–974, 1989) which is a standard neuropsychologist's pencil-and-paper test involving simple matching-to-sample skills. A commercial computerized form of this test is called the "Multidigit Memory Test," ("MDMT"; see, Nies and Sweet, "Neuropsychological assessment and malingering: A critical review of past and present strategies", *Archives of Clinical Neuropsychology*, Vol. 9, No. 6, pp. 501–552, Nov. 18, 1994). These tests are directed more to memory deficit malingering than true memory testing, since suspected malingerers, but not real organic amnestics, "do poorly" on them.

In the conventional MDMT, there are 3 blocks of trials. The protocol for each trial in a block is as follows: A subject faces a computer screen. Every 5–20 seconds a 5-digit sample number appears on the screen for about 3 seconds. The sample onset is accompanied by a 2-tone (each an octave apart) signal. Then, there is a delay interval of 2 seconds. (In Block II, the interval is 7 seconds and in Block III, the interval is 15 seconds). This interval is followed by a test to see if the subject remembers the original sample number. That is, there are 3 blocks of 24 trials each, with the first block having a short interval ("easy" task—2 second), the second block being "harder" with 7 second delays, and the third block being "hardest" with 15 second delays.

The test of memory on the conventional MDMT involves presentation on a display screen, after the delay intervals, of the correct 5-digit match on one side (right or left) and a mismatch on the other side, along with instructions to the subject to press one key or another to indicate right or left as his choice of the matching number. The side where the match appears varies randomly across trials. Immediately after the choice, the signal "right" or "wrong" is presented, accompanied by a sustained (about 1 second) high tone for "right," or a rapid (1 second) sequence of 5 low tones for "wrong".

Before the second and third blocks, the subject gets the message "You're doing great, now let's make it harder!" This is really an entrapment attempt, because normal subjects as well as almost all but the most grossly damaged actual but non-malingering head-injured patients perform at near 100% correct on all blocks of this test. However, suspected patient malingerers and experimentally instructed, malingering normal subjects do relatively "poorly" on this test, especially on the "harder" blocks. The blocks are all easy for all persons, even those with head injury.

Other, similar tests for determining simulated memory deficiency include the Fifteen-Item Test and the Hiscock Forced-Choice Procedure. These tests, and others, are described in "Detecting Simulated Memory Impairment: Comparison of the Rey Fifteen-Item Test and the Hiscock Forced-Choice Procedure", Guilmette et al , *The Clinical Neuropsychologist*, 8, 283–294 (1994).

Although these tests may be useful in many circumstances, they fall short of correctly identifying all malingering subjects with certainty. Neuropsychologists tend to take poor scores (percent correct) on such tests as evidence of malingering. Of course, it is difficult to be absolutely certain that a poor behavioral score provides this evidence, since some legitimately injured person could produce a low score. Thus the test score, by itself, is of limited value. It is typically one of many results which a neuropsychologist, neurologist, or psychiatrist would look at so as to render an opinion about malingering.

Accordingly, there continues to be a need for a highly reliable memory test procedure to determine whether or not a person is malingering memory impairment,

SUMMARY OF THE INVENTION

The present invention comprises a method and system for detecting memory deficiency malingering in a subject, The subject is presented with a series of trials wherein each trial includes display of a sample stimulus, followed by display of a test stimulus. In some of the trials the test stimulus matches the sample stimulus and in others of the trials the test stimulus does not match the sample stimulus, The subject's brain waves are measured and recorded during at least some of the display of the test stimuli. The subject indicates with respect to at least some of the test stimuli whether the test stimulus matches or does not match the sample stimulus. Memory deficiency malingering can be determined by comparing the verbal indication from the subject to the measured brain waves of the subject.

BRIEF DESCRIPTION OF THE DRAWING

FIG. 5b illustrates the display screen of FIG. 1 showing a matching test stimulus for the sample number of FIG. 5a.

FIG. 6b illustrates the display screen of FIG. 1 showing mismatch test stimulus for the sample number of FIG. 6a.

DETAILED DESCRIPTION OF THE PRESENTLY PREFERRED EMBODIMENTS

Figure 1:
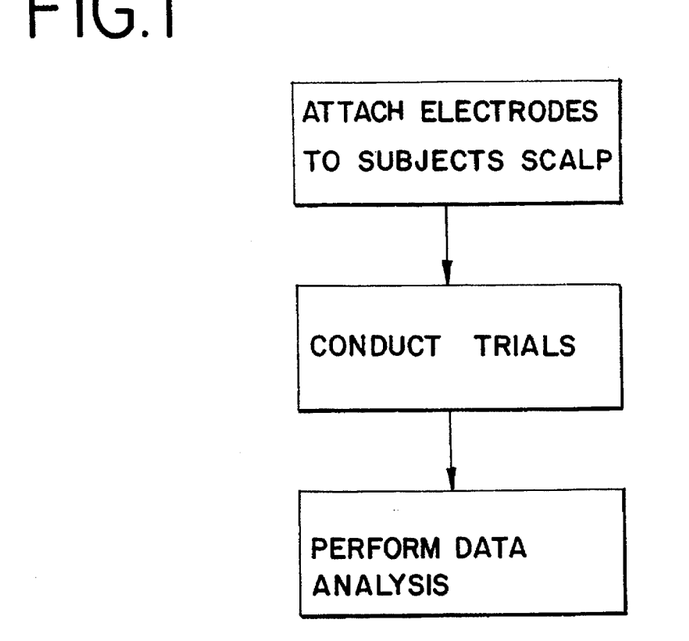
FIG. 1 is a flow chart of a program for performing an embodiment of a malingering test according to a first embodiment of the present invention.

Referring to FIG. 1, there is a flow chart illustrating implementation of a malingering test according to an embodiment of the present invention. The embodiment of the malingering test involves three steps: First, test equipment is attached to a subject for the purpose of measuring and recording the subject's brain waves. Next, a series of trials are conducted with the subject while the subject's brain waves are recorded. Following the series of trials, the brain wave data are analyzed whereby a determination of the subject's memory ability can be made.

Figure 2:
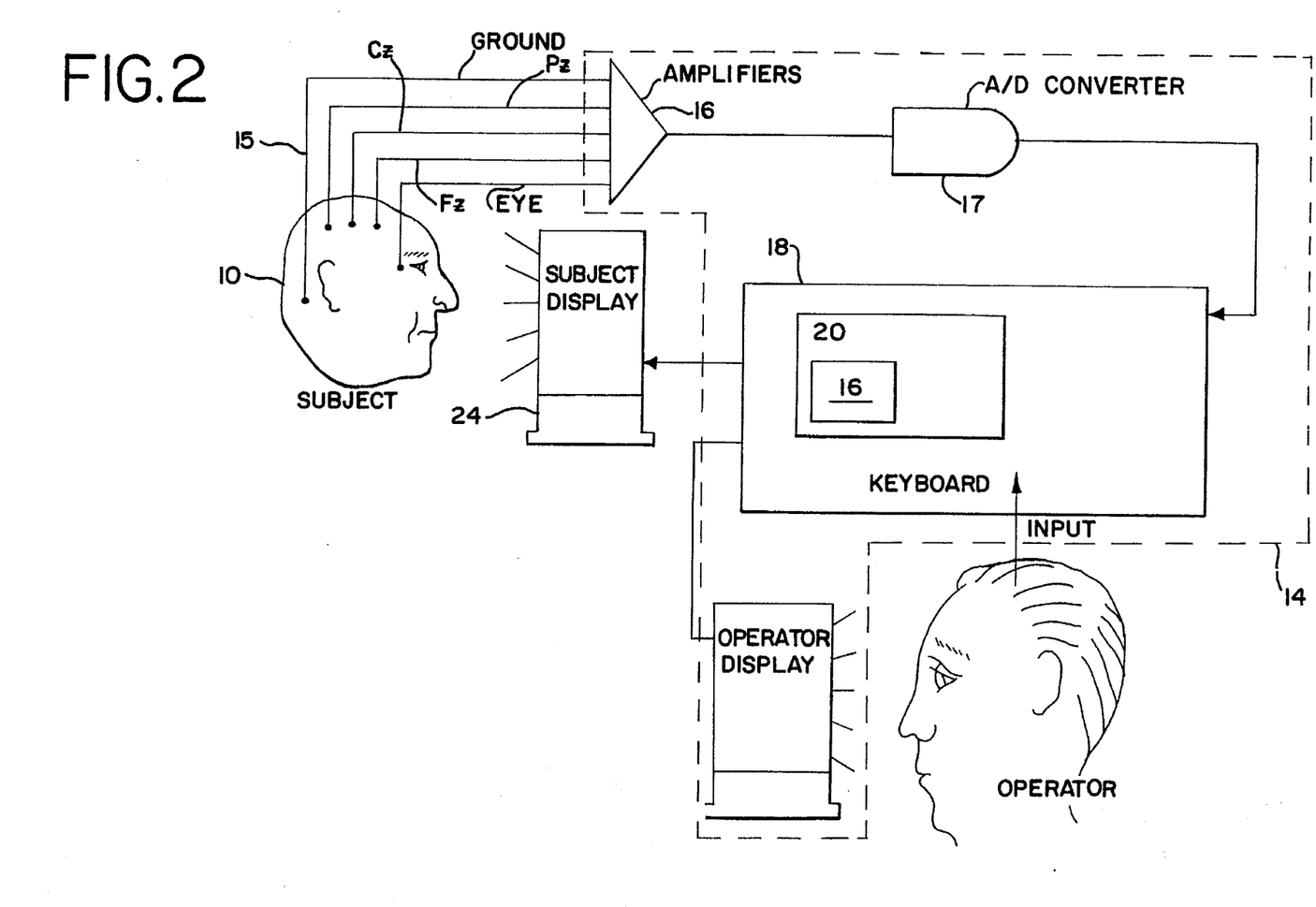
FIG. 2 is a schematic representation of a subject and test equipment using the method of FIG. 1.

Referring to FIG. 2, there is illustrated an arrangement for connecting a subject to the brain wave measuring and recording equipment. According to this embodiment, a subject 10 to be tested is connected to EEG sensing and recording equipment 14. The EEG sensing and recording equipment 14 is designed to sense and record the subject's brain waves, in particular P300 type event-related-potentials (ERP's). Specifically, the subject's Pz, Cz, Fz values are sensed and stored, and the P300 (or P3) response is examined. The recording methods are described in published papers, (see Rosenfeld, Angell, et al., "An ERP-based control question lie detector analog: Algorithms for discriminating effects within individual waveforms", *Psychophysiology*, 28, 320–336, 1991; and Johnson & Rosenfeld, "A new ERP-based deception detector analog II: Utilization of non-selective activation of relevant knowledge", *Int J. Psychophysiology*, 12, 289–306, 1992), and are also described in U.S. Pat. Nos. 4,932,416 and 5,113,870. The disclosures of these two papers and two patents are specifically incorporated herein by reference.

According to one acceptable method, silver—silver chloride electrodes 15 are attached with conductive EEG paste to Fz, Cz and Pz scalp sites. Linked mastoids are the references with the forehead grounded. Electrodes are also placed supra- and sub-orbitally for EOG recording; i.e., eye movement artifacts occurring during the recording epoch are detected and trials containing 80 µV or higher deflections are discarded and replaced. Signals are amplified 75,000 times by Grass P511-K or similar preamplifiers 16 with 3 db filters set to pass signals between 0.1 and 30 Hz. Conditioned signals are led to 8-bit analog/digital converters 17 sampling one point every 8 ms, and then to a microcomputer 18 for on-line analysis and data storage. As explained in more detail below, recording begins 104 milliseconds prior to item presentation and ended 1.944 seconds later. Some off-line digital filtering of ERP's is described below.

Once the subject 10 is connected to the brain wave sensing and recording apparatus 14, the trials portion of the test for malingering is conducted. In a preferred embodiment, the trials portion of the malingering test is conducted utilizing the same computer 18 that used to operate the EEG testing and recording equipment 14, although in alternative embodiments more than one computer may be utilized. In the present embodiment, the computer 18 runs a program 20 that includes the malingering test 16 that includes procedures for acquiring and recording the brain wave data, conducting the trials, and analyzing the data. The program 20 that is run on the computer is written in a suitable programming language, such as BASIC, C, or assembly. A copy of the source code for an exemplary program 20 is included in the appendix of this specification.

For the trials portion of the malingering test, a display 24 is utilized. The computer 18 is connected to the display 24 which is located relative to the subject 10 so that the output of the display 24 is easily observable by the subject 10. In a preferred embodiment, the computer 18 is an IBM clone.

The trials portion of the memory test 16 is composed of a session in which the subject is presented with a series of trials 30. In one embodiment of the memory test 16, the series of trials may include 100–300 trials. The trials may be divided into groups or blocks of trials with each block composed of approximately 100 trials so that a memory test 16 of 100 trials may be composed of a single block of 100 trials, a memory test of approximately 200 trials may be composed of two blocks having 100 trials per block, and a memory test of approximately 300 trials may be composed of three blocks, and so on.

On each trial, the subject 10 is shown first a sample number on the display 24, followed by a brief interval, and next shown a test stimulus number on the display 24. In each trial, the test stimulus number is either a match or a mismatch to the sample number. The pattern of match and mismatch trials is random within the series of trials. Generation of the random sample numbers and the stimulus numbers is performed by the program 16 and may be done prior to running the trials on the subject or may be performed while the trials are being conducted. The EEG sensing and recording equipment 14 measures and records the subject's EEG response during display of the stimulus number. Each single brain response is separately recorded and stored on the computer 20.

Following display of the stimulus number, the subject is required to indicate whether the stimulus number matches the sample number. The subject's indication, e g "yes" or "no" is recorded This ends a single trial. Following the subject's indication, the subject is presented with another trial in which the series of steps are repeated. Of course, on the next the trial, the new randomly generated test number is likely to be different.

Figure 3:
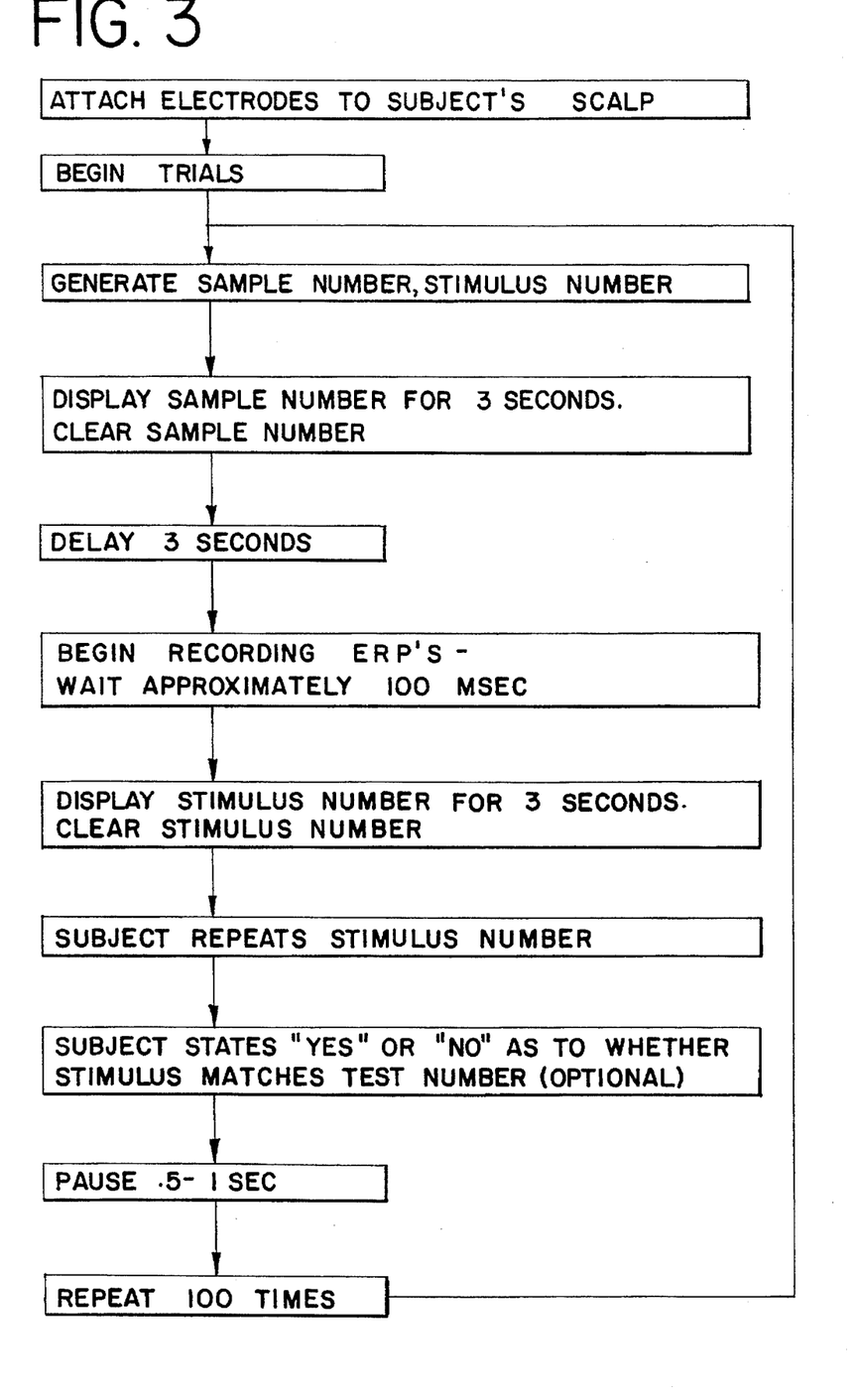
FIG. 3 is a flow chart showing program flow for conducting a trial as part of the program of FIG. 2.
Figure 4:
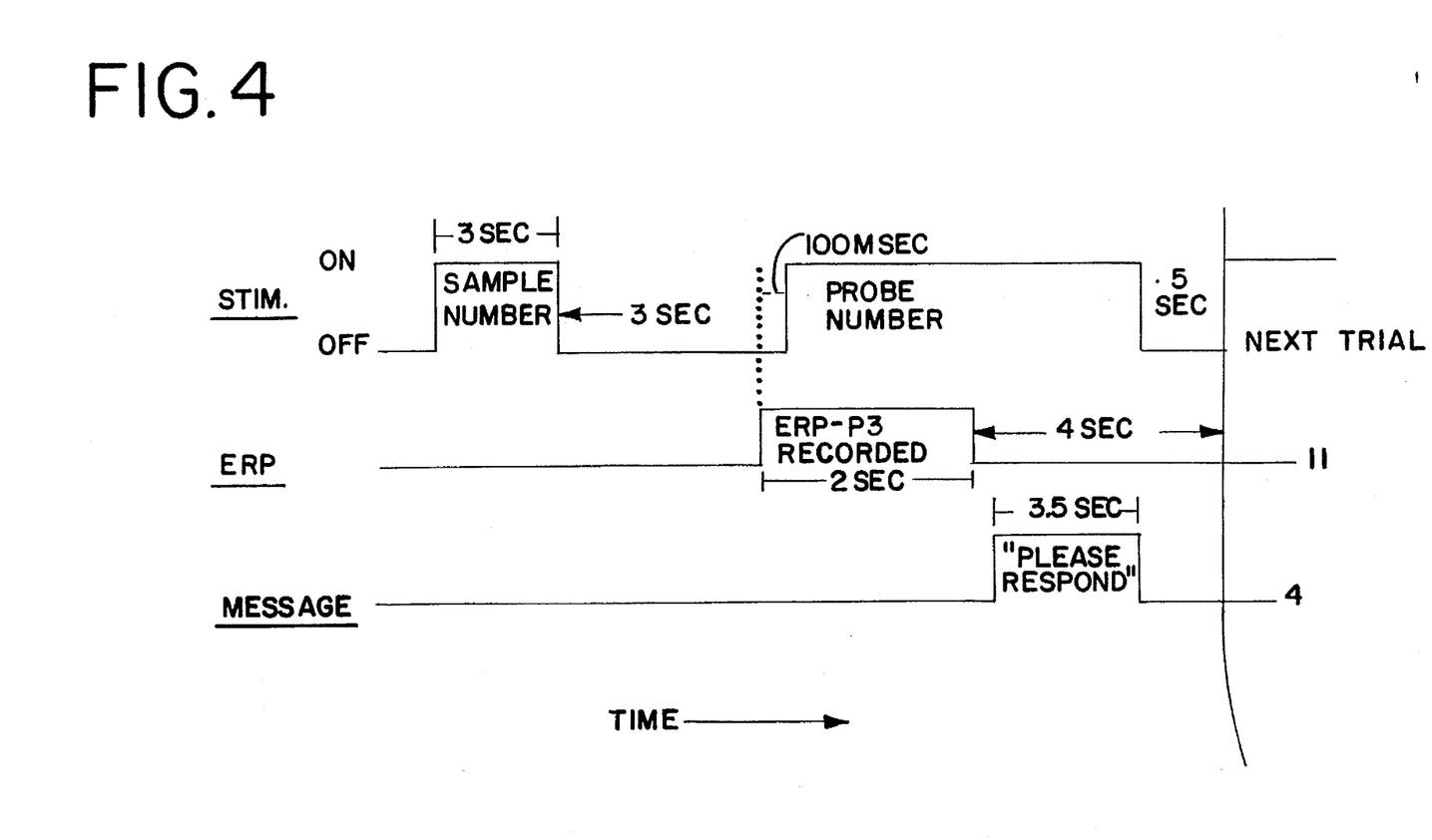
FIG. 4 an event graph illustrating the time onset of activities in one the trial represented in FIG. 2.

The above-described method is set forth in the following sequence of steps that occurs in each trial, and with reference to FIGS. 3 and 4:

1. A sample number is presented on the display 24 in such a manner that it is observable by the subject 10. The subject has been previously instructed to repeat the sample number aloud as soon as he sees it. The sample number is displayed for 3 seconds after which the sample number is cleared.

2. A delay interval of 3 seconds occurs.

3. The EEG test equipment 14 begins recording the subjects ERP.

4. One hundred milliseconds after step 3, a test stimulus is presented on the display 24 so that it is observable by the subject 10. The test stimulus number is displayed for 3 seconds and cleared. ERP recording ends.

5. The subject indicates, e.g. by saying "yes" or "no," whether the test stimulus was a match or mismatch to the sample number.

6. On some or all of the trials, the subject 10 is required to repeat the stimulus number. The subject is required to respond in 1–2 seconds.

7. The subject is signaled "right" or "wrong" with accompanying sound effects.

8. Wait 0.5 to 1 seconds, then go to Step 1 and begin next trial.

The above series of steps constitutes a single trial and, as mentioned above, the trials portion of the malingering test includes a series of such trials, e.g. 100–300, to be presented to the subject.

Figure 5A:
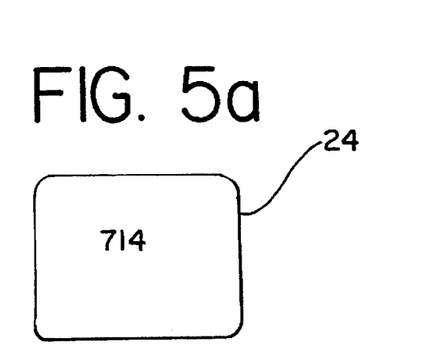
FIG. 5a illustrates the display screen of FIG. 1 showing one sample number.
Figure 5B:
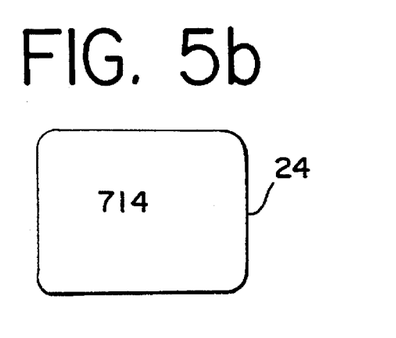
Figure 6A:
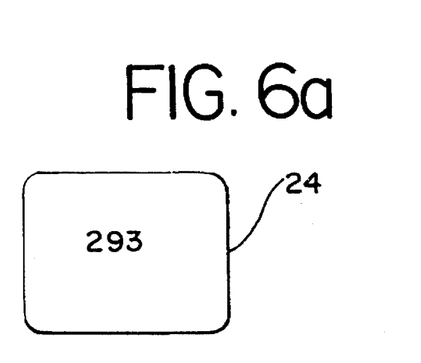
FIG. 6a illustrates the display screen of FIG. 1 showing another sample number.
Figure 6B:
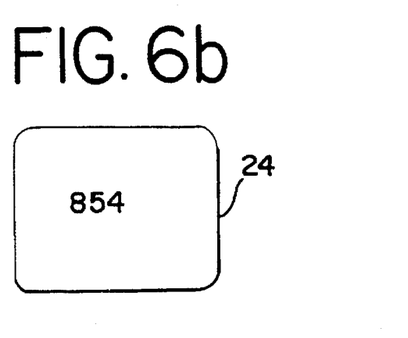

As mentioned above, in each trial, the stimulus number either matches or does not match the previously displayed sample number. A match trial is illustrated in FIGS. 5a and 5b wherein the stimulus number "714" shown in FIG. 5b is a match to the sample number shown "714" in FIG. 5a. A mismatch trial is illustrated in FIGS. 6a and 6b wherein the stimulus number "854" shown in FIG. 6b does not match the sample number "293" shown in FIG. 6a.

Including the subject's "yes" or "no" indication on each trial, the four possible trial combinations are:

1) match-right (MR). The sample number and the stimulus number are a match and the subject correctly identifies the sample number and the stimulus number as a match.

2) match-wrong (MW). The sample number and the stimulus number are a match and the subject incorrectly identifies the sample number and the stimulus number as a mismatch.

3) mismatch-right (SR). The sample number and the stimulus number are a mismatch and the subject correctly identifies the sample number and the stimulus number as a mismatch.

4) mismatch-wrong (SW). The sample number and the stimulus number are a mismatch and the subject incorrectly identifies the sample number and the stimulus number as a match.

In this embodiment, the subject is instructed to repeat the sample number aloud as soon as he sees it. This forces the subject to pay attention to the sample number. For the same reason, the subject is instructed to repeat the stimulus number aloud, but not immediately. The critical ERP recording is time-locked to and mostly in response to the stimulus number. Since speech during the ERP recording could produce artifacts in the ERP, the subject is instructed and practiced in withholding this repetition of the stimulus number until after 1948 milliseconds of post-test-number ERP (to the stimulus number) recording are over. The stimulus number remains on the subject's screen until the ERP recording time expires. Then the subject's screen is cleared, which is his signal to repeat the stimulus number. Having the subject repeat either the sample number or the stimulus number is for purposes of assuring that he is paying attention. Other means may be used to assure that the subject pays attention to the test.

In addition to artifacts caused by speech during ERP recording, eyeblinks, movements, etc. during ERP recording can also produce artifacts which distort EEG data. Therefore, whenever an artifact is detected the trial is replaced and the data removed (as in Rosenfeld et al., 1991). Since artifact rates up to 50% may be tolerable, as many as 200 trials need to be run to yield 100 clean trials with 20 matches. Greater than 200 trials may produce boredom, drowsiness, etc., and are preferably avoided. Accordingly, 100–150 trials per block is preferred.

As mentioned above, the EEG sensing and recording equipment 14 collects EEG values from about 100 milliseconds prior to presentation of the stimulus number to 1948 milliseconds after clearing of the stimulus number. Initially, each single brain wave response for one trial is digitally filtered to remove noise greater than 2–10 Hz.

For the sample numbers and test stimulus numbers, it has been determined that 3-digit numbers work better than 5-digit numbers in producing P300 effects. Enhanced P3 effects have been found from insuring that on a mismatch trial, no single digit in the stimulus number repeats any digit in the sample number.

According to the present embodiment, it has been determined that the sample number should be displayed for a duration of 2–3 seconds and that the duration that the stimulus number should be displayed is also 2–3 seconds. The preferred interval between clearing the display of the sample number and presentation of the stimulus number on the display is 2–3 seconds, with 3 seconds being most preferred although up to 5 seconds is also satisfactory.

Within a block of trials, match trial frequencies of 15–50% have been used, i.e. in 100 trials there would be 15–50 matches and 85–50 mismatches. While the lower match probabilities (15–30%) yield the best results, values as great as 50% may be effective in producing a greater match than mismatch amplitude in many subjects. Matches tend to produce P300 responses by virtue of the fact that they are matches. However the fact that the low probabilities produce best results suggests that there may also be an "oddball-like" effect operating also, meaning that rare events tend to produce P300. Since the aim here is diagnosis, both effects are utilized and 15–25% match probabilities are employed. Since statistical reliability tests require about 20 match trials, a total of at least 100 artifact-free trials should be obtained.

DATA ANALYSIS

In addition to conducting the trials and collecting the data, the memory test 16 also includes an analysis of the data collected during the series of trials. Various analytical and statistical techniques may be employed in a manner that is well known in the art.

First, to compare effects (i.e., match versus mismatch) on P3 or P300, in one analytic method, only Pz data are utilized since P3 is maximum at Pz. (Data from other scalp sites may also be analyzed and may improve diagnostic accuracy.) Two methods of measuring P3 amplitude may be utilized. The standard baseline-to-peak (b-p) method and the peak-to-peak (p—p) method. It is expected that the p—p measure yields the best diagnostic outcomes and is preferred. Other methods in addition to these may be used.

In the standard baseline-to-peak (b-p) method, the program 20 calculates the value of each 104 msec segment (13 data points) of waveform in the interval from 472 to 1200 ms. It then subtracts the maximum positive segment from the average value of the pre-stimulus baseline, i.e., of the 13 points (104 milliseconds) of sampled ERP preceding probe stimulus onset. This value is the baseline-to-peak (b-p) value. The time following stimulus of the midpoint of the maximum segment is taken as the P3 latency.

Figure 7:
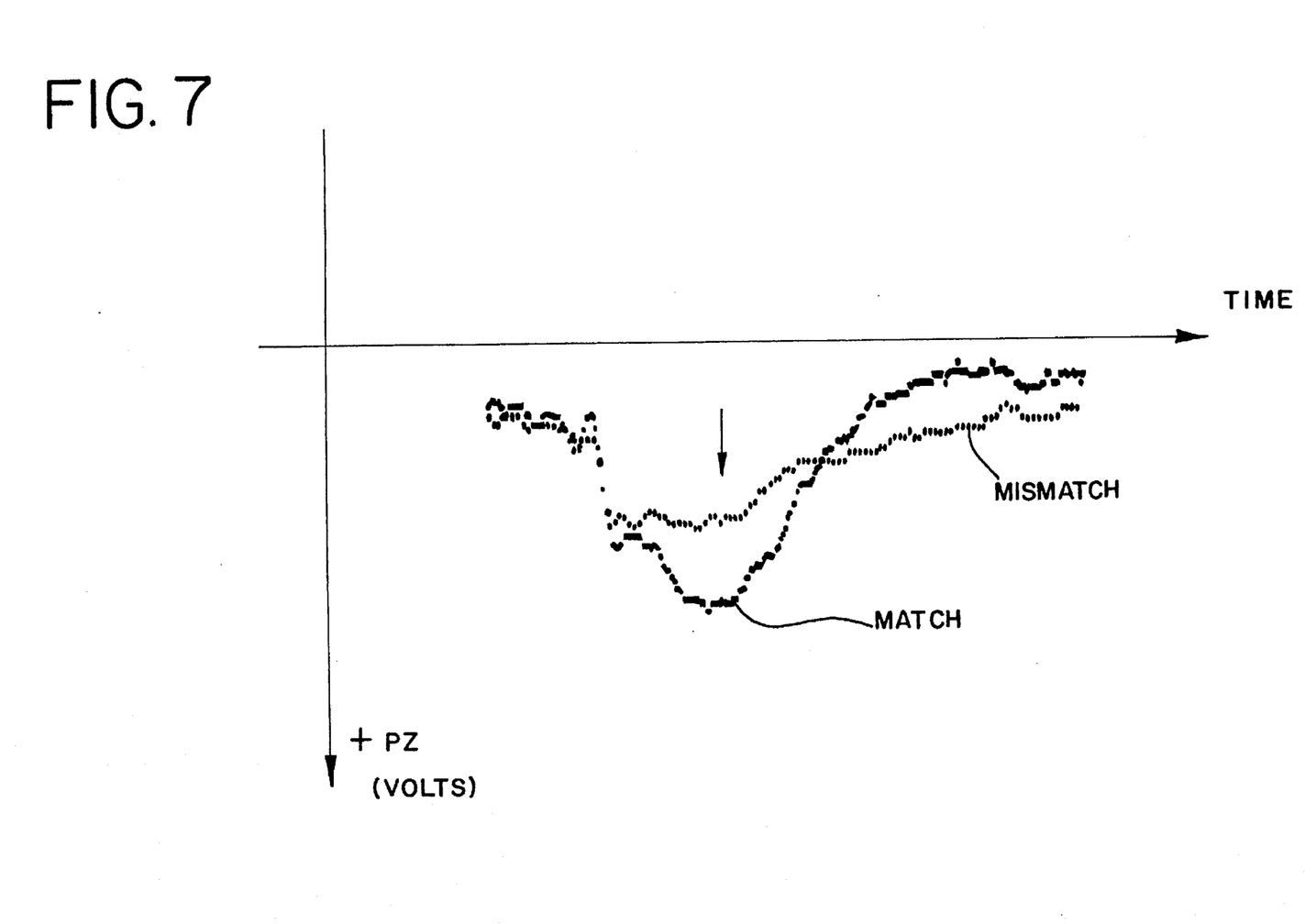
FIG. 7 is a graph showing an event related potential (ERP) brain wave pattern associated with a match overlaid with a brain wave pattern associated with a mismatch illustrating the observable difference.

In the second method of P3 amplitude determination, the peak-to-peak (p—p) method, the program 20 finds the maximum positive segment from 472 to 1200 milliseconds, as above, but subtracts it from the subsequent maximum negative segment, which it finds by determining the maximum negative 104 millisecond segment in the interval from the previously found P3 latency to the end of the sweep. This negativity is seen in FIG. 7. The arrow points to the P3 peak (down-going, by convention), and it is seen that on recovery from P3, the ERP goes above (up-going/negative) the baseline value.

There are several analytic approaches that may be used. In the present embodiment, the key question for each subject was whether or not the brain's (P3) response to the match was greater than that to the mismatch. Any reliable difference would be diagnostic, but there are theoretical reasons to predict match to be greater than mismatch on the basis of the fact that the match is rarer and more meaningful. Two approaches were utilized and other approaches may be used as well.

In one method, an independent groups t-test was performed. In the t-test, a comparison was made between the mean P3 response in matches with that of mismatches. To do this, the computer program 20 determines P3 (b-p and p—p) by examining each single sweep (i.e., each of 18 single sweeps) of a given subject for the maximum P3 (and subsequent negative component in p—p analyses), since to do a t-test each value is required.

It is preferable to minimize the risk that the single sweep method used in t-tests might pick up a noise peak as a signal peak, particularly in ERP's with expectedly small P3's; e.g., mismatch waves. Accordingly, prior to doing a t-test on each subject, a simple digital low-pass filter algorithm is applied to the entire set of single sweeps: its 3 db down point is about 4–5 Hz. It is noted that the independent groups (vs correlated) t-test is appropriate since although all waveforms in a set are from one person, there are no correlation patterns due to random order of match-mismatch presentation over time in the block.

The other method that may be utilized to determine if the match P3 mean exceeds the mismatch mean within an individual is the bootstrap method. (Wassermann & Bockenholt, "Bootstrapping: Applications to psychophysiology", *Psychophysiology*, 26, 208–221, 1989) which has been previously utilized in P3 research (e.g., Rosenfeld et al., "An ERP-based control-question lie detector analog: Algorithms for discriminating effects within individual waveforms", *Psychophysiology* 1991; Farwell & Donchin, "The truth will out: Interrogative polygraphy ("lie detection") with event-related potentials", *Psychophysiology*, 28, 531–547, 1991; Johnson & Rosenfeld, "A new ERP-based deception detector analog II: Utilization of non-selective activation of relevant knowledge", *Int J. Psychophysiology*, 12, 289–306, 1992). The bootstrap variation utilized here proceeds as follows. After digitally filtering the single sweep set (matches and mismatches) for a subject, as described above, the computer program 20 goes through the match set and draws at random but with replacement a set of n waveforms. It averages these and calculates P3 from this single average using the maximum segment selection method described above. Then a set of n waveforms is drawn randomly with replacement from the mismatch set, and a mismatch average P3 is calculated. Bootstrapped means are based on a number approximately corresponding to the match trials (e.g. n=18 where the percentage of match trials is 17% of a total of 108 trials). The calculated mismatch mean P3 is subtracted from the comparable match value, and one thus obtains a difference value to place in a bootstrapped distribution which will contain 100 values after 100 iterations of the process just described. Iterations will yield differing (variable) means and mean differences due to the sampling-with-replacement process. In order to state with relatively high confidence that match and mismatch are indeed different, one requires that the value of zero difference not be within +1.96 standard deviations from the mean of the standardized bootstrapped distribution. Bootstrapping's validity rests on the ability of the bootstrapped distribution to allow a good estimation of the population variance of the average P3 value, when only one average of several single sweeps is available for a given subject (Wasserman & Bockenholt, above). It is noted that other bootstrap methods may be used (e.g., Farwell & Donchin, above; Honts & Devitt "Bootstrap decision making for polygraph examination: Final report of DOD/PERSEREC Grant No. N0014-92-1794, Psychology Department, University of North Dakota, Grand Forks, (1992)). Alternatively, Bayesian statistical and factor-analytic approaches may be used (Allen et al., "The development and validation of an event-related potential memory assessment procedure: A methodology for prediction in the face of individual differences", *Psyophysiology*, 29, 504–522, 1992).

It is noted that the two methods described have differing advantages. The t-test may utilize more mismatch data than will the bootstrap approach. However, since bootstrapping involves repeated averaging, it will tend not to erroneously pick noise peaks in single sweeps as P3 values.

Data analysis shows that the P300 amplitude for the match trials is larger than the P300 for the mismatch trials. Also, the analysis shows that P300 latency variance for the true, non-malingering, head injured subjects is larger than the normative values. Thus, a subject whose latency variance looks normal, and whose P300 response amplitude to the match exceeds that to the mismatch, but whose behavioral performance is poor is a likely malingerer, i.e. his brain suggests that he can tell matches from mismatches and that the latency of the P300 is not as variable as that which are now observed in real head-injured subjects.

Alternative Embodiments

In the embodiment described above, the memory test is composed of one block of approximately 100 trials. In an alternative embodiment, the test may consist of two blocks of trials with 100 trials in each block. In this alternative embodiment, the subject is instructed in both blocks to repeat the sample number aloud as soon as he sees it as in the first embodiment. This forces him to attend to the sample number. For the same reason, also, in both runs, the subject must repeat the test number aloud, but not immediately. The critical ERP recording is time-locked to and mostly in response to the test stimulus number. Since speech during the ERP recording could produce artifacts in the ERP, the subject is instructed and practiced in withholding this repetition of the test stimulus number until after 1948 milliseconds of post-test-number ERP (to the test stimulus number) recording are over. The test number remains on the subject's screen until the ERP recording time expires. Then the subject's screen is cleared, which is his signal to repeat the test stimulus number.

The two blocks would differ in that in one block ("ERP only") the subject does only what was just described, whereas in the other run ("verbal response"), the subject additionally says aloud "yes" or "no" for match and mismatch respectively, just before repeating the test stimulus and just after the test stimulus is cleared from the screen. This furnishes evidence of malingering by providing both 1) evidence that the subject is behaving (in his verbal responses) as if he cannot discriminate matches and mismatches while 2) his ERP responses indicate that he can discriminate these.

An alternative procedure for the ERP run is to use a run in which the subject repeats the sample numbers, but withholds repetitions of test numbers except on a random sample of 5–15% of test trials in which the program is interrupted and the subject asked to repeat test numbers. If he cannot do this accurately, then it is reasonable to infer he is trying to "beat the test" by not attending to test stimuli. He is, of course, warned in advance that this procedure will be followed so that he is likely to cooperate. The reason for this alternative approach is that it makes the test epoch simpler. As disclosed in U.S. Pat. No. 5,137,027, the entire disclosure of which is incorporated herein by reference), if subjects are required to do secondary tasks in P300 recording sessions, the dual test requirement diverts cognitive processing resources and the P300 amplitude is reduced. In embodiments of the present invention, the requirement of repeating test stimuli could have the same effect, which is undesirable since P300s are key indicators of match recognition. While repeating test stimuli number would appear a simple extra task, research has shown that head injury patients are particularly sensitive to dual task requirements in general. It is also known that head injury patients have smaller than normal P300s in the simplest oddball task. In order to ensure that P300s, though smaller, are present and detectable in non-malingering head injury patients (see, Ellwanger et al., "P300s to autobiographical and learned information in closed head injury patients", *Psychophysiology (Supplement)*, 31, S43, 1994) because of earlier evidence that 1) the P300s are smaller in head injury patients, 2) dual tasks are hard for head injury patients, and 3) dual tasks reduce P300s, in at least some patients, the alternative approach, where no test repetitions are required except in a fractional subset of trials, may be utilized. ERP data are not collected on these trials.

Research on normals simulating amnesia indicates that P300s in response to matches and mismatches are maximally different (the desired diagnostic effect) when subjects repeat the test stimulus and say "yes" or "no" following clearance of the test stimulus from the screen. A study on non-malingering, actual head injury patients, compared P300 responses in "repeat only" blocks with P3 responses in "repeat and say "yes" or "no" blocks. As with normals, the P3 was bigger when a decision was required.

In a further alternative embodiment, three blocks of trials could be employed. If three blocks of trials are used, the interval of time between clearing the display of the sample number and presentation of the test stimulus number could be set to different durations for each of the three blocks. For example, in a first block of 100 trials the interval could be 2 seconds, in a second block of 100 trials the interval could be 3.2 seconds, and in the third block of 100 trials the interval could be 5 seconds.

It is noted that alternative variants of this entire procedure are possible in which acoustic rather than visual stimuli are used. Further, words, patterns, etc., rather than numbers are utilized.

It is intended that the foregoing detailed description be regarded as illustrative rather than limiting and that it is understood that the following claims including all equivalents are intended to define the scope of the invention.

I claim:

1. A method for memory malingering detection in a subject comprising:

presenting a series of trials to the subject wherein each trial includes display of a sample stimulus, followed by display of a test stimulus, wherein in some of the trials the test stimulus matches the sample stimulus and in others of the trials the test stimulus does not match the sample stimulus;

measuring brain waves of the subject at least during the display of some of the test stimuli to the subject;

receiving an indication from the subject with respect to at least some of the test stimuli whether the test stimulus matches or does not match the sample stimulus and;

detecting likelihood of memory malingering by the subject based upon the indication from the subject and the measured brain waves of the subject.

2. The method of claim 1 wherein the sample stimulus and the test stimulus are numbers.

3. The method of claim 1 wherein the series of trials includes at least approximately 100 trials.

4. The method of claim 1 wherein the series of trials includes up to three blocks of trials with each block having approximately 100 trials.

5. The method of claim 1 in which the subject is required with respect to at least some of the trials to repeat aloud the sample stimulus.

6. The method of claim 1 in which the sample stimulus is displayed for approximately 3 seconds.

7. The method of claim 1 further comprising:

providing a delay interval of approximately 3 seconds between cessation of display of the sample stimulus and start of display of the test stimulus.

8. The method of claim 1 in which measuring of the brain waves begins before display of the test stimulus.

9. The method of claim 1 in which measuring of the brain waves begins approximately 100 milliseconds before display of the test stimulus.

10. The method, of claim 1 in which the test stimulus is displayed for approximately 3 seconds.

11. The method of claim 1 in which the subject is required with respect to at least some of the trials to repeat aloud the test stimulus.

12. The method of claim 1 further comprising:

signaling to the subject whether the indication by the subject is correct or incorrect.

13. The method of claim 1 further comprising:

filtering at least some of the brain waves to remove noise.

14. The method of claim 1 in which the sample stimulus is a three digit number.

15. The method of claim 1 in which the sample stimulus is a number having between three and five digits.

16. The method of claim 1 further comprising:

in at least some of the trials in which the test stimulus does not match the sample stimulus, providing a test stimulus in which no single digit of the test stimulus matches any digit of the sample stimulus.

17. The method of claim 1 wherein the percentage of trials in the series of trials in which the test stimulus matches the sample stimulus is approximately 15–50%.

18. The method of claim 1 wherein the percentage of trials in the series of trials in which the test stimulus does not match the sample stimulus is approximately 50–85%.

19. The method of claim 1 wherein the percentage of trials in the series of trials in which the test stimulus matches the sample stimulus is approximately 15–25%.

20. The method of claim 1 further comprising:

with respect to some of the trials of the series of trials, requiring the subject to repeat the test stimulus.

21. The method of claim 1 in which the series of trials includes some trials in which a duration of time between display of the sample stimulus and display of the test stimulus is a first interval and other trials in which the duration of time between display of the sample stimulus and display of the test stimulus is a second interval, different from the first interval.

22. The method of claim 21 in which the series of trials includes still other trials in which a duration of time between display of the sample stimulus and display of the test stimulus is a third interval, different from the first and second intervals.

23. The method of claim 22 in which the first interval is approximately 2 seconds, the second interval is approximately 3.2 seconds, and the third interval is approximately 5 seconds.

24. The method of claim 1 in which the sample stimulus and the test stimulus are patterns.

25. The method of claim 1 in which the sample stimulus and the test stimulus are words.

26. The method of claim 1 further comprising the step of diagnosing memory malingering in the subject based upon the indication from the subject and the measured brain waves of the subject.

* * * * *